United States Patent
Evonitz, III

(10) Patent No.: US 6,792,951 B2
(45) Date of Patent: Sep. 21, 2004

(54) BREATHABLE AIR PRESSURIZED SAFETY HELMET

(76) Inventor: Alex V. Evonitz, III, 22 Harris Dr., Carbondale, CO (US) 81623

( * ) Notice: Subject to any disclaimer, the term of this patent is extended or adjusted under 35 U.S.C. 154(b) by 440 days.

(21) Appl. No.: 10/005,723

(22) Filed: Nov. 2, 2001

(65) Prior Publication Data

US 2002/0056458 A1 May 16, 2002

Related U.S. Application Data

(60) Provisional application No. 60/245,906, filed on Nov. 3, 2000.

(51) Int. Cl.[7] ................................................ A61F 11/00
(52) U.S. Cl. ................ 128/857; 128/858; 244/122 AG; 2/424; 2/171.3
(58) Field of Search ................................. 128/857, 858, 128/859, 863; 244/122 AG, 121; 2/410, 171, 424, 171.3

(56) References Cited

U.S. PATENT DOCUMENTS

| | | | |
|---|---|---|---|
| 3,362,403 A | | 1/1968 | Fleming et al. ............. 128/142 |
| 4,054,953 A | | 10/1977 | De Barsy ....................... 2/414 |
| 4,126,131 A | | 11/1978 | Davis et al. ................. 128/142 |
| 4,549,541 A | | 10/1985 | Sundahl ........................ 128/201 |
| 4,575,875 A | * | 3/1986 | Dawson et al. ................ 2/424 |
| 4,581,775 A | * | 4/1986 | Nava ............................... 2/424 |
| 4,584,721 A | * | 4/1986 | Yamamoto ...................... 2/424 |
| 4,918,752 A | * | 4/1990 | Briggs ............................ 2/424 |
| 5,039,035 A | * | 8/1991 | Fitzpatrick ........... 244/122 AG |
| 5,156,145 A | | 10/1992 | Flood et al. ................. 128/201 |
| 5,365,615 A | * | 11/1994 | Piszkin ........................... 2/424 |
| 5,991,930 A | * | 11/1999 | Sorrentino ..................... 2/424 |
| 6,112,333 A | * | 9/2000 | Mazzei ........................... 2/410 |
| 6,250,299 B1 | | 6/2001 | Danisch et al. ............. 128/201 |

OTHER PUBLICATIONS

Provisional application, Breathable Air Pressurized Safety Helmet, 60/245,906, dated Nov. 2, 2000, 5 pages and 2 drawings.

* cited by examiner

*Primary Examiner*—Fadi H. Dahbour
(74) *Attorney, Agent, or Firm*—Santangelo Law Offices, P.C.

(57) ABSTRACT

Helmet protection methods and systems designed to protect the wearer from not only physical impact but also from non-impact safety risks posed by noxious fumes, fire, lack of oxygen, and particulate matter and the like by creating a positive pressure inside the helmet while still permitting normal human respiration, are presented. More specifically, a helmet, a compressed air canister(s) such as a cartridge or a tank, for example, sensor(s) that may trigger an pressurized air release element that may initiate a flow of breathable air from the canister(s), and an exfiltration mechanism that may permit the increase of air pressure within the helmet such that safety endangering conditions (such as noxious fumes, heat buildup, particulate matter and the like) are prevented from entering inside the helmet but respiration by the human wearer is still possible, are presented.

32 Claims, 2 Drawing Sheets

BREATHABLE AIR PRESSURIZED SAFETY HELMET

RELATED APPLICATIONS

This application claims the benefit of U.S. Provisional Application No. 60/245,906 filed Nov. 3, 2000, hereby incorporated by reference.

BACKGROUND OF THE INVENTION

The ongoing concerns for driver safety in racing have not included a fundamental of life-sustaining, breathable air in the condition of fire or fumes. This is the guiding principal of the Breathable Air Pressurized Safety Helmet. Incorporating a pressure above that of atmospheric (positive pressure) that may be accomplished by the release of breathable air from a compressed air canister(s) for a time following a racing incident such as an impact or fire, the instant invention can expel potentially harmful contaminants (such as flames, heat, noxious fumes, chemicals, particulate matter, oxygen deficient air, for example) away from the head of the helmet occupant and prevent the intrusion of further contaminants. This increased pressure is key to this system and provides protection specifically when there is a possibility of toxic fumes or fire or other danger present before an individual can exit the environment. Additionally, safety personnel exposed to similar hazards could benefit from this available and supplemental air supply.

SUMMARY OF THE INVENTION

In several embodiments, this invention relates to helmet protection methods and systems designed to protect the wearer from not only physical impact but also from non-impact safety risks posed by noxious fumes, fire, lack of oxygen, and particulate matter and the like by creating a positive pressure inside the helmet while still permitting normal human respiration. The present invention is designed for application in a car, or other powered vehicle environment, but may also be applied in other environments such as perhaps air flight where dangerous conditions such as those mentioned above may arise or even in any environment that may pose the danger of the release of harmful chemicals, heat, flames, noxious odors or gases, or oxygen deficient air, and the like. The present invention may involve a helmet, a compressed air canister(s) such as a cartridge or a tank or other type of container, sensors that may trigger an release element that may initiate a flow of breathable air from the canister(s), and exfiltration components that may permit the increase of air pressure within the helmet such that safety endangering conditions (such as noxious fumes, heat buildup, particulate matter and the like) are prevented from entering inside the helmet but respiration by the human wearer is still possible.

DESCRIPTION OF THE DRAWINGS

The accompanying drawings illustrate embodiments of the invention. In the drawings.

DETAILED DESCRIPTION OF THE INVENTION

Figure 1:
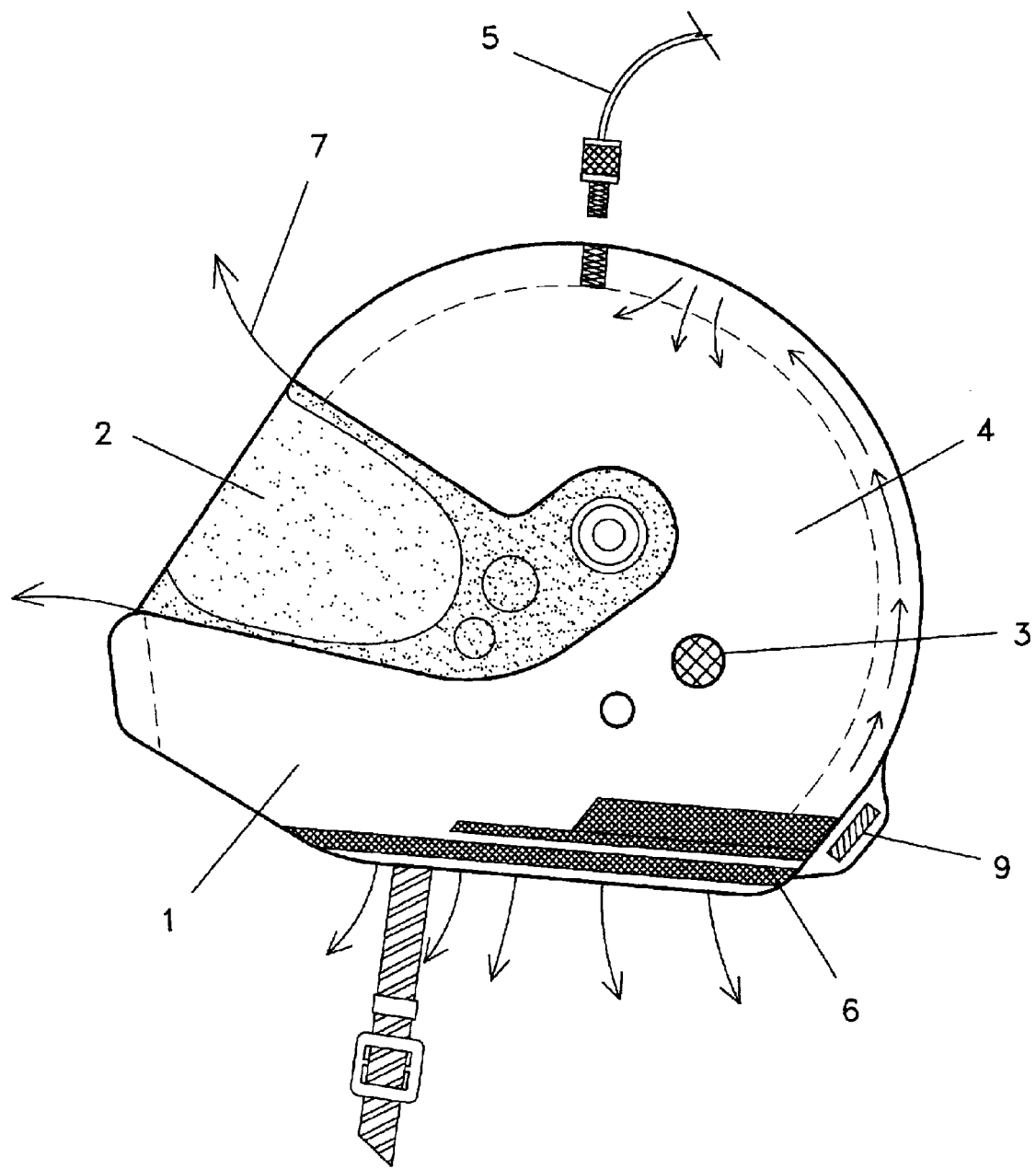
FIG. 1 is an illustration of a side view of one embodiment of the breathable air pressurized safety helmet in which there is both an outboard compressed breathable air canister (perhaps a tank, not shown) and an onboard breathable compressed air cartridge.

This helmet related protection system could simulate a short-term, self-contained breathing apparatus for individuals involved in motor sports, or person in hazardous environments. These individuals could be drivers or other safety personnel or workers. A positive pressure may be created by release of compressed air in response to the sensed presence of dangerous condition(s). Such conditions would typically be caused by vehicle impact but also may be caused by other factors such as an on-board fire, mechanical breakdown, or simply poor circulation of air in the vicinity of the driver's cage or operating area. The invention may comprise a helmet that may include an outer shell (1), a transparent face shield (2) that may be pivotally positioned, and a cushioning inside liner that would offer protection to the wearer in the event of a collision. A positive pressure created inside the helmet relative to pressure outside the helmet could operate to expel and prevent the introduction inside the helmet of dangerous contaminants such as noxious fumes, fire, particulate matter, and the like.

By means of a sensor (may be human or non-human, where non-human is defined more generally as automatic) purposefully and repeatedly assessing the presence of a dangerous condition(s), a release of air into the helmet cavity could be initiated soon after the determination of the presence of a dangerous condition. The sensor is defined generally to include any element that reacts to the presence of a stimulus—in this case that stimulus could be impact, heat, flames, noxious fumes or gases, or deficient oxygen or any other condition that poses a hazard to the wearer or the helmet. The sensor could be a human such as an occupant of a vehicle like the of the helmet or instead a person located off the vehicle as in a racing pit at a racing track or instead a worker or his or her assistant in any hazardous environment. The vehicle may be a car, boat or other powered machine such as a plane, but a vehicle is not required. The sensor may also be a sensing device that is electrical, mechanical or electromechanical in operational and may be a heat sensor, an impact sensor, an oxygen sensor, a particulate matter sensor, a fire sensor, a smoke sensor, a humidity sensor, and the like. Safety risk factor sensing refers to a searching for the presence of a safety risk factor. It could be accomplished by any sensor as defined herein and includes, among others, a passive mechanical impact sensor that reacts to impact generated forces and signals somehow (mechanically or otherwise) the air release element to release air. Upon the determination by the sensor of the presence of a safety risk factor (such as, for example, impact, fire, smoke, particulate matter, low oxygen levels, and the like) a sensor(s) could communicate with and thus activate (electrically, mechanically, via radio waves or infrared, electromechanically or the like) an air release element to initiate a release of breathable air from a compressed air canister.

The air release element may contain a remote wireless sensor signal receipt element that is able to receive a remote wireless signal from, for example, a sensor located on or off the vehicle, and initiate a release of air upon receipt of that signal. Thus, a flow of air could be released upon receipt of a wireless signal.

Alternatively, a manually operable switch or button (3) or the like located within reach of a human could be activated to electrically or mechanically or electromechanically or otherwise initiate the release of compressed air into the helmet cavity upon a human's determination of the presence of a dangerous condition(s), either by direct sensing or by indication of a sensor or by indication of an element that communicates with a sensor. A wireless sensor signal receipt element could also be located in or on the helmet, or in the vicinity of the helmet wearer, or in the vicinity of anyone acting as sensor so as to signal the sensor's determination of the presence of a dangerous condition to the wearer of the helmet. The receiver of the signal could contact the helmet wearer (if the receiver is not the wearer) so that the wearer may activate the air release. Such contact could be made wirelessly by R/F (radio frequency) or the like. The receiver of the signal could electrically, mechanically, electromechanically, or wirelessly or otherwise activate the air release mechanism.

If the system is used in a driving environment, the human sensor may be located on a vehicle or off. If located off the vehicle, he could communicate with and activate the air release element (thereby initiating a release of air from a canister) remotely via, for example, wireless communication such as radio waves as previously stated. He or she may, upon receipt of a signal from an on-vehicle sensor that a dangerous condition arises, or upon noticing it him or herself, send a signal via radio frequency or infrared or the like that either signals to the driver that a dangerous condition exists and/or initiates release of compressed breathable air.

Any release or breathable air or more generally any established flow may be provided to the internal cavity (4) of the helmet by an air transport element such as a flexible tube (5). This transport element could transfer air from the compressed air canister to the inside of the helmet by protruding through the helmet's outer shell or face shield at any area, or instead could transfer air to the inside of the helmet by traveling from an air supply canister and under the bottom rim (6) of the outer shell or through a gap (7) between the face shield and the outer shell section. By not protruding through the outer shell or face shield but instead through a gap under the helmet, for example, as mentioned, the structural integrity of the helmet would not be compromised.

A predetermined amount of air leakage designed into the helmet could insure that a safe, breathable air supply could be provided. The criteria for time and volume necessitating this air supply could be driver and situation dependent, though standards may evolve with testing. The air transport element could also be detachable from the helmet or from its connection with the compressed air canister, allowing quick removal by personnel arriving on the scene after an incident and thereafter replacement of the low or empty air canister with a full tank of compressed breathable air. Additionally there may be connected to the helmet a port or air transport element acceptor whose purpose would be to accept an air transport element attached by personnel arriving on the scene after an incident.

Figure 2:
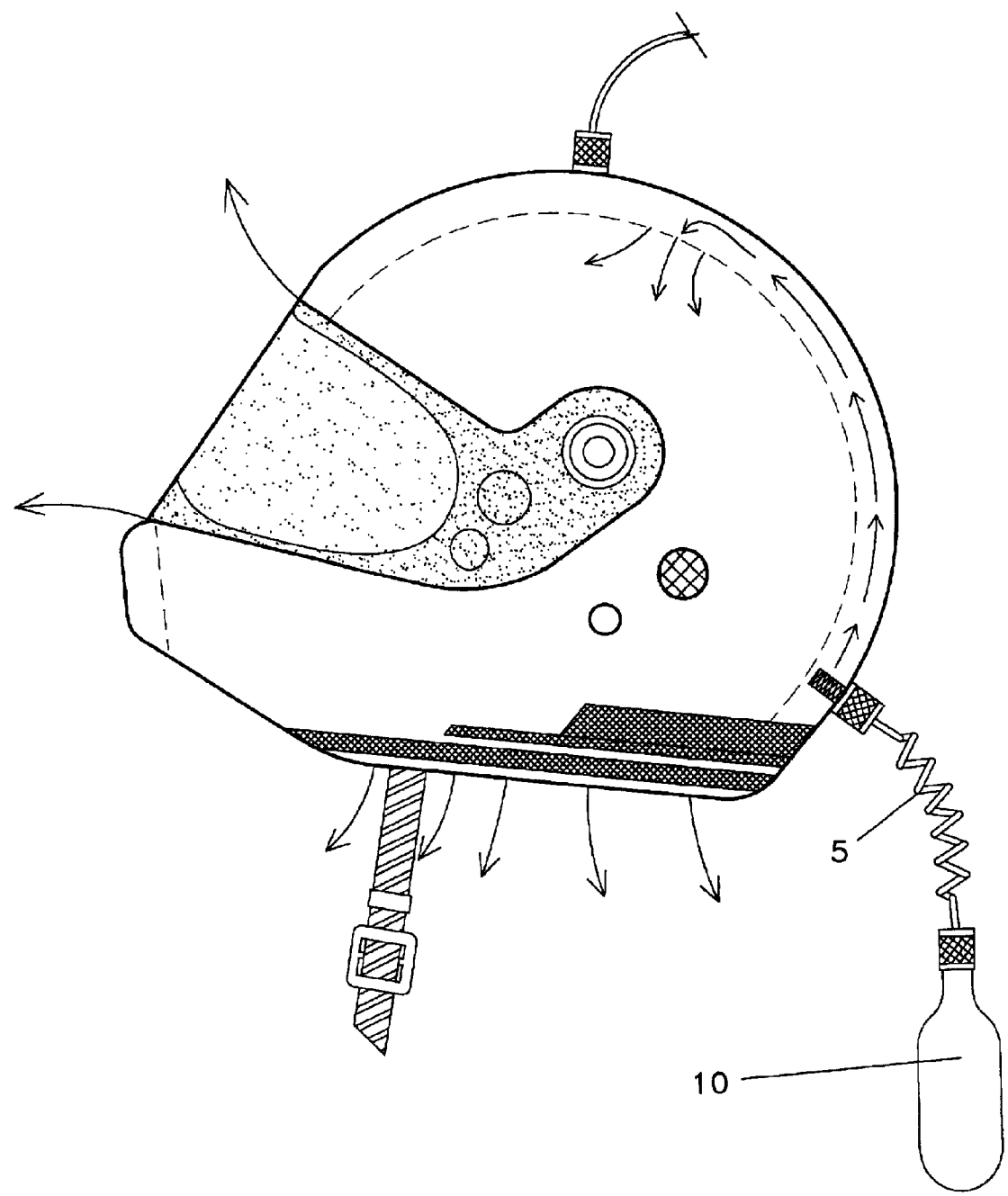
FIG. 2 is a drawing of a side view of one embodiment of the breathable air pressurized safety helmet in which there is both an outboard compressed breathable air canister (perhaps a tank, not shown) and an outboard breathable compressed air canister (a cartridge).

Installation of these system components could be outboard implying mounted to something other than the helmet and/or onboard mounted to the safety helmet itself. A small-pressurized cartridge (9) with the air release element may be part of the onboard system while outboard systems may comprise a larger tank and could provide a longer sustained airflow. A cartridge may also be provided outboard as illustrated in FIG. 2 (10) alone or in addition to an outboard tank. The release element operational on the cartridge may or may not be battery powered or it may simply be mechanical in operation.

The term canister may include any type of container capable of holding compressed gas. Air, as used herein, is defined to include any breathable gas, which is defined as suitable for respiration by a human such as pure oxygen, for example. Gas includes any gas, either breathable or non-breathable. The air transport element (labeled supplemental air/oxygen connector in FIGS. 1 and 2) is shown as connected at the top of the helmet, but may instead be connected at the sides or at an outer shell portion located below a face shield, or instead the air transport element may enter the inside of the helmet under its lower rim or through any other gap.

Pressure differentials above atmospheric necessary for safe exfiltration are yet to be determined. The pressure would have to be sustainable, such that with normal human breathing a positive exfiltration from the safety helmet system could be maintained. By exfiltrating or exfiltration is meant allowing some air and or gas to escape or exit at least some portion of the volume defined by the outer shell and the face shield. A certain amount of exfiltration could allow the buildup of an internal pressure above an ambient value (the value of gas pressure outside of the helmet) that is sufficient to exclude from and prevent the introduction into the internal cavity of the helmet dangerous contaminants, yet still allow human respiration (specifically enabling the introduction of "new" breathable air from the pressurized canister(s) and the eradication of waste carbon dioxide respiration gases). Exfiltration may be through an exfiltration or venting element(s) such as a flexible shroud (may be adjustable) located along the bottom rim (6) of the helmet and/or through vents or punctures (or more generally holes) located anywhere on the helmet and/or through a unitary pressure regulator located anywhere on the helmet and/or along the edges of the border of the transparent face shield with the outer shell. Exfiltration through the gap between the helmet wearer and the bottom rim of the helmet may also occur without a flexible shroud. Pressure regulation may be accomplished by any of these exfiltration elements. The outboard system could provide higher airflow and greater pressures for longer periods but the means of providing a connection might be cumbersome. Such a connection could include generally an air transport element, such as, for example, a flexible tube (5) as shown in FIGS. 1 and 2. A cartridge may also provide breathable air to the inside of the helmet via an air transport element, or may directly release air inside the helmet without using an air transport element.

A retrofit system for existing safety helmets might also be a viable option. Further, onboard systems may provide interior protection to the head from injury in the form of a cartridge safety element should the user experience an unexpected cartridge failure. The exterior of the onboard mounting could be a partial outer shell blow-off assembly thus further reducing the chance of injury from explosive cartridge releases, or instead there could be provided between the cartridge and the head of the helmet wearer some type of barrier that would further protect the wearer.

Providing the option of manual pressurization could accommodate events in which a driver remains conscious, with dexterity. A simple mechanical device initiated from a convenient helmet location, or remotely could be available. Operation by the user or safety personnel could then provide a further or alternate level of protection. Connections from outboard air supplies could also enhance protection during increased levels of exposure.

Combinations of the onboard and outboard system could provide a next tier of safe air. In the event the system triggers, an onboard system could provide immediate protection while a supplemental outboard system was activated. Other persons working in areas of fueling or fire filled environments could also gain a significant level of protection from this positive pressure system. The invention instead may involve only an onboard system or only an outboard system.

As can be easily understood from the foregoing, the basic concepts of the present invention may be embodied in a variety of ways. It involves both pressurized air techniques as well as pressurized safety helmet design to accomplish the appropriate air management. In this application, the pressurized air techniques are disclosed as part of the results shown to be achieved by the various devices described and as steps which are inherent to utilization. They are simply the natural result of utilizing the devices as intended and described. In addition, while some device designs are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims maybe included to address the functions the invention and each element performs. Neither the description nor the terminology is intended to limit the scope of the claims included in this full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by the disclosure.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of an "air release element" should be understood to encompass disclosure of the act of "releasing air" —whether explicitly discussed or not—and, conversely, were there only disclosure of the act of "releasing air", such a disclosure should be understood to encompass disclosure of an "air releasing mechanism", and even a "means for releasing air". Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent or other information statements filed with the application are hereby incorporated by reference, however, as to each of the above, to the extent that such information or statements incorporated by reference might be considered inconsistent with the patenting of this/these invention(s) such statements are expressly not to be considered as made by the applicant (s).

Thus, the applicant(s) should be understood to have support to claim at least: i) an air providing device as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced for such systems or components, ix) methods and apparatuses substantially as described hereinbefore and with reference to any of the accompanying examples, and x) the various combinations and permutations of each of the elements disclosed. In this regard it should be understood that for practical reasons and so as to avoid adding potentially hundreds of claims, the applicant may eventually present claims with initial dependencies only. Support should be understood to exist to the degree required under new matter laws—including but not limited to United States Patent Law 35 USC 132 or other laws—to permit the addition of any of the various dependencies or other elements presented under one independent claim or concept as dependencies or elements under any other independent claim or concept. Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

What is claimed is:

1. A helmet system for the protection of a wearer comprising:
   a) a protective head covering, comprising
      i) an outer shell adapted to cover a substantial portion of said wearer's head;
      ii) a transparent face shield connected to said outer shell; and
      iii) a cushioning element inside of said outer shell;
   and defining a protective head covering cavity;
   b) at least one compressed breathable supply gas canister fluidicly coupled to said protective head covering;
   c) at least one safety risk factor sensor;
   d) a gas release element fluidicly coupled to said at least one compressed breathable supply gas canister and responsive to said safety risk factor sensor so as to release breathable supply gas into said protective head covering cavity upon the sensed presence of a safety risk factor; and e) at least one pressurized gas exfiltration element substantially fixed relative to said protective head covering.

2. A helmet system for the protection of a wearer as in claim 1 wherein said at least one compressed breathable supply gas canister comprises a cartridge.

3. A helmet system for the protection of a wearer as in claim 2 wherein said cartridge is directly attached to said outer shell.

4. A helmet system for the protection of a wearer as in claim 2 wherein said helmet system further comprises a cartridge failure safety element.

5. A helmet system for the protection of a wearer as in claim 1 wherein said at least one compressed breathable supply gas canister comprises a tank located externally to said outer shell.

6. A helmet system for the protection of a wearer as in claim 1 wherein said compressed breathable supply gas canister is fluidicly coupled to a location within said protective head covering by a gas transport element.

7. A helmet system for the protection of a wearer as in claim 6 wherein said gas transport element comprises a detachment element.

8. A helmet system for the protection of a wearer as in claim 1 wherein said safety risk sensor comprises at least one impact sensor.

9. A helmet system for the protection of a wearer as in claim 1 wherein said gas release element comprises at least one manually operable element.

10. A helmet system for the protection of a wearer as in claim 1 wherein said gas release element comprises at least one electrically activatable element.

11. A helmet system for the protection of a wearer as in claim 1 wherein said gas release element comprises a remote wireless signal response element.

12. A helmet system for the protection of a wearer as in claim 1 wherein said gas release element comprises at least one mechanically activatable element.

13. A helmet system for the protection of a wearer as in claim 1 wherein said at least one pressurized gas exfiltration element comprises a flexible shroud attached along a base rim of said protective head covering.

14. A helmet system for the protection of a wearer as in claim 1 wherein said at least one pressurized air exfiltration element comprises a pressurized gas exfiltration element located at substantially the border of said face shield with said outer shell.

15. A helmet system for the protection of a wearer as in claim 1 wherein said at least one pressurized gas exfiltration element comprises at least one hole in said outer shell.

16. A helmet system for the protection of a wearer as in claim 1 wherein said pressurized gas exfiltration element comprises at least one pressure regulator.

17. A helmet system for the protection of a wearer as in claim 1 further comprising a remote wireless sensor signal receipt element.

18. A method for protecting a user comprising the steps of:
a) securing a protective head covering substantially around a user's head;
b) providing at least one compressed breathable supply gas canister fluidicly coupled to said protective head covering;
c) safety risk factor sensing;
d) determining safety risk factor presence;
e) establishing at least one flow of breathable gas from said at least one compressed breathable supply gas canister in response to said step of determining safety risk factor presence;
f) providing said at least one flow of breathable gas to inside said protective head covering in response to said step of establishing at least one flow of breathable gas;
g) increasing an internal head covering gas pressure to above an ambient condition value in response to said step of providing said at least one supply of breathable gas; and
h) exfiltrating gas from within said protective head covering through an exfiltration element in response to said step of increasing an internal head covering gas pressure.

19. A method for protecting a user as in claim 18 wherein said step of safety risk factor sensing comprises the step of automatically sensing the presence of a safety risk factor.

20. A method for protecting a user as in claim 18 wherein said step of safety risk factor sensing comprises the step human sensing the presence of a safety risk factor.

21. A method for protecting a user as in claim 18 wherein said step of establishing at least one flow of breathable gas comprises the step of manually initiating a release of said at least one flow of breathable gas by a human wearer of said protective head covering in response to said step of determining safety risk factor presence.

22. A method for protecting a user as in claim 18 wherein said step of establishing at least one flow of breathable gas comprises the step of electrically initiating a release of said at least one flow of breathable gas in response to said step of determining safety risk factor presence.

23. A method for protecting a user as in claim 18 wherein said step of establishing at least one flow of breathable gas comprises the step of establishing a flow of breathable air from a compressed breathable gas cartridge.

24. A method for protecting a user as in claim 18 wherein said step of establishing a flow of breathable gas from said compressed breathable gas canister comprises the step of initiating a release from said flow of breathable gas externally of said protective head covering.

25. A method for protecting a user as in claim 18 wherein said step of exfiltrating air from within said protective head covering comprises the step of exfiltrating gas through a flexible shroud provided at a rim located at the base of said protective head covering.

26. A method for protecting a user as in claim 18 wherein said step of exfiltrating air from within said protective head covering comprises the step of exfiltrating gas through a border defined by a transparent helmet face shield and an outer helmet shell.

27. A method for protecting a user as in claim 18 wherein said step of exfiltrating air from within said protective head covering comprises the step of exfiltrating gas through a unitary pressure regulator.

28. A method for protecting a user as in claim 18 further comprising the step of adjusting said exfiltration element.

29. A method for protecting a user as in claim 18 further comprising the step of providing a cartridge failure safety element.

30. A method for protecting a user as in claim 18 wherein said method for protecting a user is implementable in a racing vehicle environment.

31. A method for protecting a user as in claim 18 further comprising the step of replacing a gas transport element fluidicly connected to said protective head covering.

32. A method for protecting a user as in claim 18 further comprising the step of wirelessly communicating.

* * * * *